United States Patent
Eom et al.

(10) Patent No.: US 12,038,399 B2
(45) Date of Patent: Jul. 16, 2024

(54) APPARATUS AND METHOD FOR ANALYZING BIOLOGICAL MATERIAL COMPONENT, AND APPARATUS FOR MEASURING IMPEDANCE

(71) Applicants: SAMSUNG ELECTRONICS CO., LTD., Suwon-si (KR); GWANGJU INSTITUTE OF SCIENCE AND TECHNOLOGY, Gwangju (KR)

(72) Inventors: Kun Sun Eom, Yongin-si (KR); Myoung Hoon Jung, Bucheon-si (KR); Sung Yang, Gwangju (KR); Minkook Son, Gwanju (KR); Alexander Zhbanov, Gwangju (KR); Ye Sung Lee, Gwangju (KR)

(73) Assignees: SAMSUNG ELECTRONICS CO., LTD., Suwon-si (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 947 days.

(21) Appl. No.: 17/014,634

(22) Filed: Sep. 8, 2020

(65) Prior Publication Data
US 2021/0302345 A1  Sep. 30, 2021

(30) Foreign Application Priority Data

Mar. 25, 2020  (KR) .................. 10-2020-0036391

(51) Int. Cl.
*G01N 27/04*  (2006.01)
*A61B 5/053*  (2021.01)
(Continued)

(52) U.S. Cl.
CPC .......... *G01N 27/045* (2013.01); *A61B 5/053* (2013.01); *A61B 5/145* (2013.01); *G01N 27/028* (2013.01);
(Continued)

(58) Field of Classification Search
CPC .... G01N 27/045; G01N 27/028; G01N 27/07; G01N 27/22; G01N 33/48; G01N 33/49;
(Continued)

(56) References Cited

U.S. PATENT DOCUMENTS 6,169,394 B1  1/2001  Frazier et al.
7,693,561 B2  4/2010  Schrepfer et al.
(Continued)

FOREIGN PATENT DOCUMENTS

KR      10-1875417 B1     7/2018
KR    10-2018-0090597 A   8/2018
KR    10-2019-0119617 A   10/2019

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for analyzing a biological material component may include an impedance sensor comprising a first electrode having a first contact surface that contacts an analysis target, and a second electrode having a second contact surface that contacts the analysis target and that faces the first contact surface. The apparatus may include an impedance measurement assembly configured to measure impedance of the analysis target using the first electrode and the second electrode. The apparatus may include a processor configured to model the measured impedance as an equivalent circuit, and analyze a biological material component based on a modeling result.

19 Claims, 11 Drawing Sheets

(51) Int. Cl.
*A61B 5/145* (2006.01)
*G01N 27/02* (2006.01)
*G01N 27/07* (2006.01)
*G01N 27/22* (2006.01)
*G01N 33/48* (2006.01)
*G01N 33/49* (2006.01)

(52) U.S. Cl.
CPC .............. *G01N 27/07* (2013.01); *G01N 27/22* (2013.01); *G01N 33/48* (2013.01); *G01N 33/49* (2013.01)

(58) Field of Classification Search
CPC ........... A61B 5/053; A61B 5/145; A61B 5/01; A61B 5/026; A61B 5/0537; A61B 5/14532; A61B 5/14546; A61B 5/7203; A61B 5/681; A61B 5/4869; A61B 5/72
See application file for complete search history.

(56) References Cited

U.S. PATENT DOCUMENTS

| | | | |
|---|---|---|---|
| 8,032,211 B2 | 10/2011 | Hashimshony et al. | |
| 8,197,406 B2 | 6/2012 | Caduff et al. | |
| 8,200,307 B2 | 6/2012 | Caduff et al. | |
| 8,882,670 B2 | 11/2014 | Hancock | |
| 9,155,505 B2 | 10/2015 | Caduff et al. | |
| 9,179,856 B2 | 11/2015 | Caduff et al. | |
| 9,247,905 B2 | 2/2016 | Caduff et al. | |
| 9,526,431 B2 | 12/2016 | Zakharov et al. | |
| 9,549,695 B2 | 1/2017 | Caduff et al. | |
| 9,713,447 B2 | 7/2017 | Caduff et al. | |
| 9,952,135 B2 | 4/2018 | Ayliffe | |
| 9,952,169 B2 | 4/2018 | Son et al. | |
| 10,149,629 B2 | 12/2018 | Szczepaniak et al. | |
| 10,376,152 B2 | 8/2019 | Koch et al. | |
| 2007/0282180 A1 | 12/2007 | Caduff et al. | |
| 2008/0214910 A1* | 9/2008 | Buck | A61B 5/1495 600/310 |
| 2010/0075353 A1* | 3/2010 | Heaton | A61B 5/743 435/14 |
| 2010/0240977 A1 | 9/2010 | Caduff | |
| 2011/0144525 A1 | 6/2011 | Megej et al. | |
| 2011/0160554 A1 | 6/2011 | Megej et al. | |
| 2012/0035858 A1 | 2/2012 | Caduff et al. | |
| 2013/0211280 A1* | 8/2013 | Gregory | A61B 5/7203 600/547 |
| 2015/0192536 A1 | 7/2015 | Son et al. | |
| 2017/0284955 A1* | 10/2017 | Lai | G01N 27/3274 |
| 2018/0351550 A1 | 12/2018 | Degen | |
| 2019/0076070 A1 | 3/2019 | Nogueira et al. | |
| 2019/0376926 A1 | 12/2019 | Tarasov | |

* cited by examiner

APPARATUS AND METHOD FOR ANALYZING BIOLOGICAL MATERIAL COMPONENT, AND APPARATUS FOR MEASURING IMPEDANCE

CROSS-REFERENCE TO RELATED APPLICATION(S)

This application claims priority to Korean Patent Application No. 10-2020-0036391, filed on Mar. 25, 2020, in the Korean Intellectual Property Office, the entire disclosure of which is incorporated by reference herein in its entirety.

BACKGROUND

1. Field

Example embodiments relate to an apparatus and method for analyzing a biological material component using bio-impedance.

2. Description of Related Art

Various medical devices for diagnosing a health condition of a patient are being developed. In the process of diagnosing the health condition, the importance of medical apparatuses for measuring a bioelectric signal of the patient is being highlighted due to convenience of the patient and rapidity of a health diagnosis result, etc.

As bio-impedance apparatuses may be used for monitoring the health or emotional state of a living body, various studies are being conducted to manufacture a bio-impedance measuring device in a smaller size while still providing a method of measuring the bio-impedance quickly and accurately.

SUMMARY

Additional aspects will be set forth in part in the description which follows and, in part, will be apparent from the description, or may be learned by practice of the presented embodiments.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an example embodiment, an apparatus for analyzing a biological material component may include an impedance sensor comprising a first electrode having a first contact surface configured to contact an analysis target, and a second electrode having a second contact surface configured to contact the analysis target and that faces the first contact surface: an impedance measurement assembly configured to measure impedance of the analysis target using the first electrode and the second electrode; and a processor configured to model the measured impedance as an equivalent circuit, and analyze a biological material component based on a modeling result.

The impedance measurement assembly is further configured to measure impedance at a plurality of frequencies in a predefined band.

The equivalent circuit includes two or more resistors and two or more capacitors.

The processor is further configured to remove an effect of noise including at least one of a parasitic component of the impedance sensor, and polarization effects from the measured impedance.

The processor is further configured to extract one or more parameters related to characteristics of the analysis target through the modeling result.

The one or more parameters include at least one of plasma resistance, cytoplasm resistance, plasma capacitance, a cell membrane constant phase element (CPE), diagonal capacitance, and diagonal resistance.

The processor is further configured to acquire an estimate value of a biological material component by applying a predefined biological material component analysis model to the extracted one or more parameters or an amount of change in the one or more parameters relative to a reference time point.

The reference time point includes a fasting time point.

The biological material component includes at least one of blood sugar, cholesterols, triglycerides, proteins, and uric acid.

The analysis target includes blood of a subject or a sample solution that has similar physical characteristics of blood of the subject.

The impedance sensor may further comprise an inlet portion into which the analysis target is introduced, a storage portion in which the analysis target introduced through the inlet portion is stored, and an outlet portion through which the analysis target stored in the storage is discharged.

The impedance sensor may further comprise a fluid characteristic adjustment assembly configured to adjust at least one of a temperature of the analysis target and a flow rate of the analysis target.

Each of the first contact surface and the second contact surface may have a T shape.

According to an aspect of an example embodiment, a method of analyzing a biological material component may include measuring impedance of an analysis target using a first electrode having a first contact surface that contacts the analysis target, and a second electrode having a second contact surface that contacts the analysis target and that faces the first contact surface: modeling the measured impedance as an equivalent circuit: and analyzing a biological material component based on a modeling result.

The modeling the measured impedance as the equivalent circuit comprises removing an effect of noise including at least one of a parasitic component of an impedance sensor and polarization effects from the measured impedance.

The modeling the measured impedance as the equivalent circuit comprises extracting one or more parameters related to characteristics of the analysis target.

The analyzing of the biological material component comprises acquiring an estimate value of a biological material component by applying a predefined biological material component analysis model to the extracted one or more parameters or an amount of change in the one or more parameters relative to a reference time point.

The method further comprises adjusting at least one of a temperature of the analysis target and a flow rate of the analysis target.

According to an aspect of an example embodiment, an apparatus for measuring impedance may include a first electrode having a first contact surface that protrudes from the first electrode, the first contact surface being configured to contact an analysis target: a second electrode having a second contact surface that protrudes from the second electrode, the second contact surface being configured to contact the analysis target: and an impedance measurement assembly configured to measure impedance of the analysis target using the first electrode and the second electrode.

The apparatus further comprises a fluid characteristic adjustment assembly configured to adjust at least one of a temperature of the analysis target and a flow rate of the analysis target.

Other features and aspects will be apparent from the following detailed description, the drawings, and the claims.

BRIEF DESCRIPTION OF THE DRAWINGS

The above and other aspects will be more apparent from the following description of example embodiments taken in conjunction with the accompanying drawings, in which.

DETAILED DESCRIPTION

Figure 1:
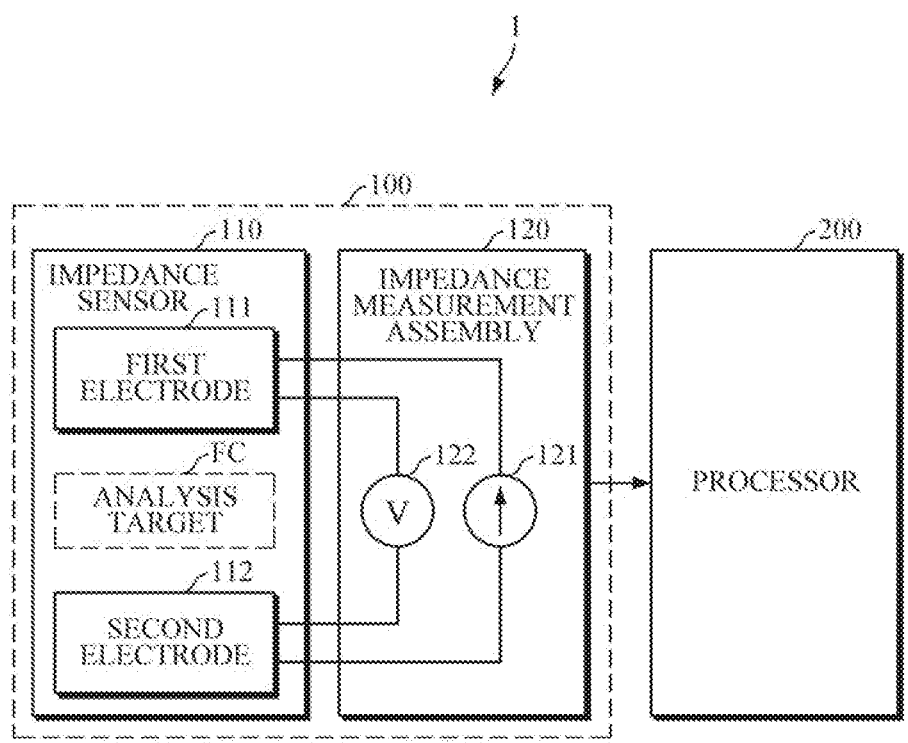
FIG. 1 is a block diagram illustrating an apparatus for analyzing a biological material component according to an example embodiment.

Advantages and features of example embodiments will be more clearly understood from the following detailed description, with reference to the accompanying drawings. Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

It will be understood that, although the terms "first," "second," etc. may be used herein to describe various elements, these elements should not be limited by these terms. These terms are only used to distinguish one element from another. Any references to the singular form of a term may include the plural form of the term unless expressly stated otherwise. In addition, unless explicitly described to the contrary, an expression such as "comprising" or "including" will be understood to imply the inclusion of stated elements but not the exclusion of any other elements. Also, the terms, such as "part," "unit," or "module," etc., should be understood as a unit that performs at least one function or operation and that may be embodied as hardware, software, or a combination thereof.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, embodiments of the apparatus and method for analyzing the substance composition in the body will be described in detail with reference to the drawings.

Figure 2:
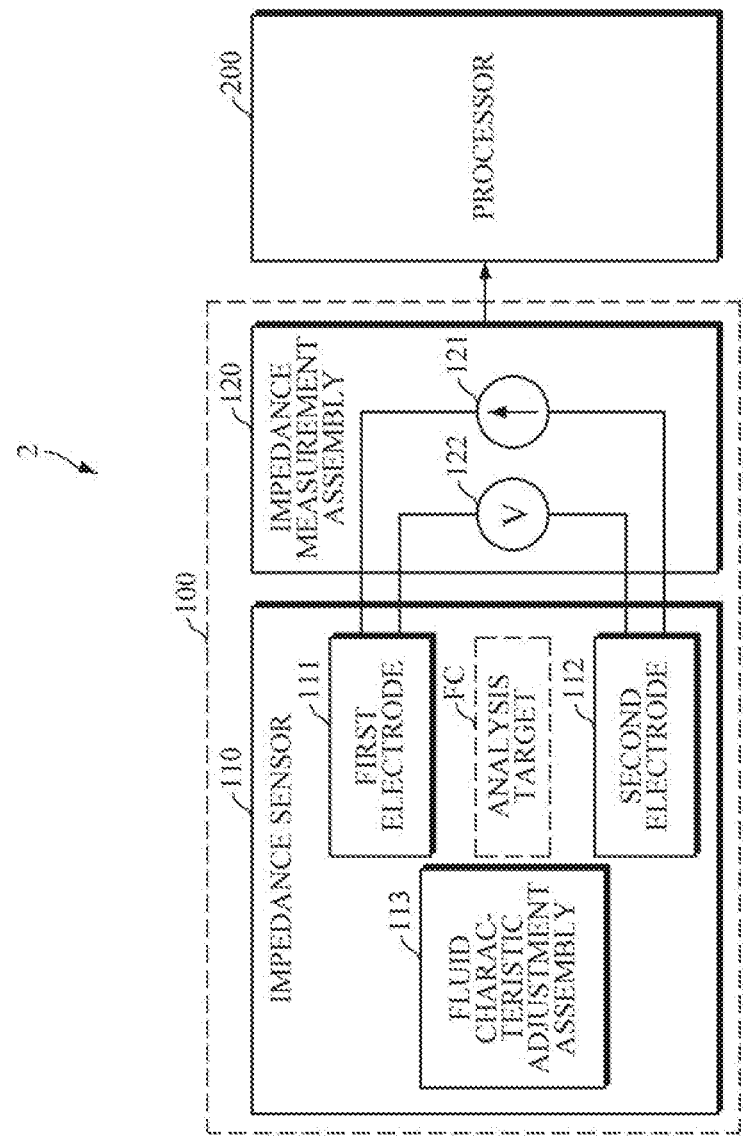
FIG. 2 is a block diagram illustrating an apparatus for analyzing a biological material component according to an example embodiment.

FIG. 1 is a block diagram illustrating an apparatus for analyzing a biological material component according to an example embodiment. FIG. 2 is a block diagram illustrating an apparatus for analyzing a biological material component according to an example embodiment. FIGS. 3A to 3D are diagrams for describing a structure of an impedance sensor according to an example embodiment. The apparatuses 1 and 2 for analyzing a biological material component according to the example embodiments may be mounted in a device in a specialized medical institution, a wearable device (e.g., a smart watch worn on a wrist, a smart band-type wearable device, a headphone-type wearable device, a hair-band type wearable device, or the like), a mobile device (e.g., a smartphone), a tablet personal computer (PC), or the like.

Referring to FIG. 1, the apparatus 1 for analyzing a biological material component includes an impedance sensor 110, an impedance measurement assembly 120, and a processor 200. The components 110, 120, and 200 of the apparatus 1 may be configured as a single piece of hardware. However, the present disclosure is not limited thereto, such that the impedance sensor 110 and the impedance measurement assembly 120 may be configured as separate pieces of hardware to form an impedance measurement device 100 and may be electrically connected directly to the processor 200 or mutually connected to the processor 200 through wired or wireless communications.

The impedance sensor 110 includes a first electrode 111 and a second electrode 112. The first electrode 111 and the second electrode 112 may be disposed on a body substrate, and the first electrode 111 and the second electrode 112 may be disposed to face each other such that the first electrode 111 is in contact with one side of an analysis target object FC and the second electrode 112 is in contact with the other side of the analysis target object FC. In this case, the analysis target object may include blood of a subject. However, the analysis target object is not limited thereto and may include a sample solution that is simulated to have similar physical characteristics as the actual blood of a subject.

The first electrode 111 and the second electrode 112 may be configured to enable impedance measurement using a two-electrode method or a four-electrode method. When impedance is measured using a two-electrode method, the first electrode 111 and the second electrode 112 may each be formed of one electrode. In addition, when impedance is measured using a four-electrode method, the first electrode 111 and the second electrode 112 may each include an input electrode used to apply a current or a constant voltage and an output electrode used to measure a voltage or current imposed on the analysis target object by the current or constant voltage applied to the input electrode. The first electrode 111 and the second electrode 112 may be formed to have various shapes, without limitation, such as a rod shape, a semicircle shape, a circular shape, and the like.

FIG. 1 illustrates two electrodes 111 and 112, but the number of electrodes is not limited thereto. For example, a third electrode and a fourth electrode may be further included. In this case, the impedance sensor 110 may be formed such that the first electrode 111 and the second electrode 112 measure impedance by a four-electrode method and the third electrode and the fourth electrode may measure impedance by a two-electrode method.

The impedance measurement assembly 120 may apply a current or a constant voltage to the first electrode 111 and the second electrode 112, and may measure a voltage or current imposed on the first electrode 111 and the second electrode 112 to measure bio-impedance. For convenience of description, a method of applying a current and measuring a voltage will be described as an example.

As shown in FIG. 1, the impedance measurement assembly 120 may include a current source 121 for applying an alternating current and a voltmeter 122 for measuring a voltage.

The impedance measurement assembly 120 may acquire impedance spectrum data by measuring a plurality of impedances while changing the frequency of an input current in a predetermined band (e.g., 1 kHz to several hundred MHz).

The impedance measurement assembly 120 may use a battery embedded in a main body of the apparatus 1 for analyzing a biological material component as a current source. Alternatively, the impedance measurement assembly 120 may be able to use the power of an external device when connected via a wired or wireless connection and supplied with the power from the external device.

Referring to FIG. 2, the apparatus 2 for analyzing a biological material component according to another embodiment includes an impedance sensor 110, an impedance measurement assembly 120, and a processor 200. The impedance sensor 110 may include a first electrode 111, a second electrode 112, and a fluid characteristic adjustment assembly 113. The first electrode 111 and the second electrode 112 of the impedance sensor 110, the impedance measurement assembly 120, and the processor 200 have been described with reference to FIG. 1, and thus descriptions thereof will not be reiterated herein.

The fluid characteristic adjustment assembly 113 may adjust the characteristics of an analysis target by taking into account various conditions, such as a type of a biological material component, the purpose of analysis, an analysis environment, such as ambient temperature, and the processing performance of the apparatus 2 for analyzing a biological material component. The characteristics of the analysis target may include temperature, flow rate, flow velocity, and the like, but is not limited thereto. Accordingly, the fluid characteristic adjustment assembly 113 may include a temperature controller, a flow rate controller, a flow velocity controller, and the like. For example, when impedance is measured in an in-vitro environment, the temperature of a fluid of the analysis target object FC may be adjusted to be similar to the temperature inside a human body.

Figure 3A:
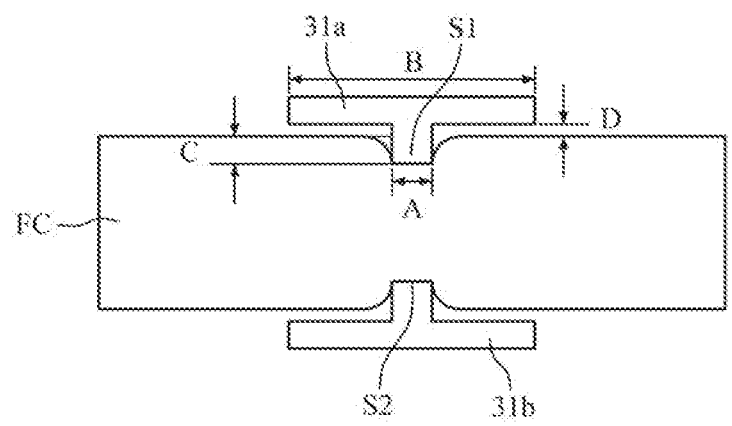
FIGS. 3A to 3D are diagrams for describing a structure of an impedance sensor according to an example embodiment.

Referring to FIG. 3A, a first electrode 31a and a second electrode 31b of an impedance sensor 110 are disposed on a main body substrate to face each other. As shown in FIG. 3A, the first electrode 31a and the second electrode 31b may, respectively, have contact surfaces S1 and S2 that are formed such that a portion of a surface facing each other protrudes in the shape of T to reduce the contact areas of the electrodes exposed to the analysis target object. An insulating film may be formed on, or an insulating material may be applied to, portions other than the contact surfaces S1 and S2 of the first electrode 31a and the second electrode 31b so as to function as an insulating layer.

In FIG. 3A, a variable A denotes a length of an exposed contact surface of an electrode, a variable B denotes an inner length of a substrate (e.g., printed circuit board (PCB)), a variable C denotes a thickness of an electrode, and a variable D denotes a thickness of an electrode insulating layer. In general, it can be understood that as variable A increases, resistance R of impedance decreases and capacitance C of impedance increases. Therefore, it can be understood that as variable B increases, the capacitance C of impedance increases. In addition, it can be understood that parasitic component capacitance Cs, which is an internal component of a device, increases with an increases of variable C and the capacitance C of impedance decreases with an increase of variable D.

Figure 3B:
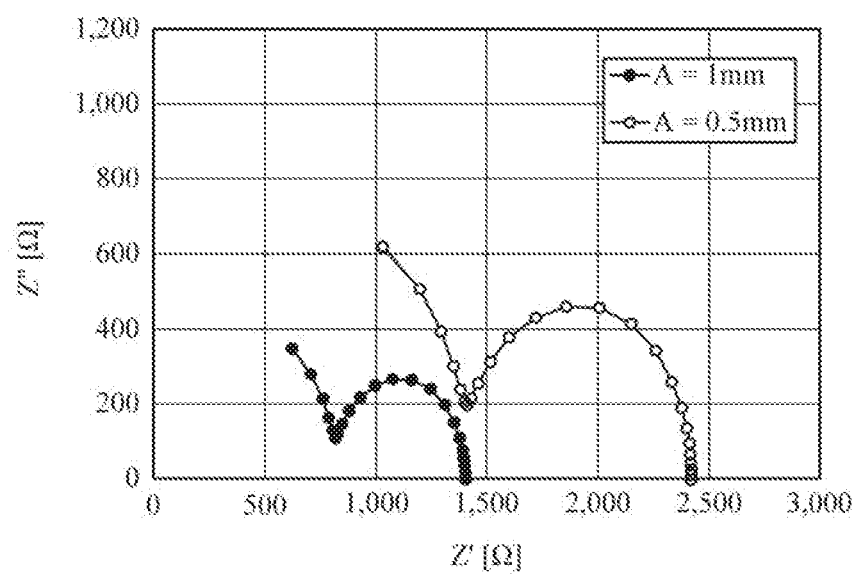

The impedance sensor 110 of the embodiments may be configured to simultaneously increase the resistance R and the capacitance C of measured impedance so that a small amount of electrical property change according to a change in blood sugar can be measured as an impedance change of a larger value. FIG. 3B shows measured impedance when variable A is 1 mm and 0.5 mm, and it can be seen that a decrease in the contact surface of the electrode in contact with the analysis target object corresponds to an increase in the measured impedance. Accordingly, the impedance sensor 110 may be configured to reduce variables A and D, and increase variable B of the first electrode 31a and the second electrode 31b.

For example, the impedance sensor 110 may be configured such that variable A has a minimum length of 20 μm when considering the size of blood cells, variable B ranges from a minimum of 20 μm to a maximum of 6 mm when considering the total length of a channel, and D has a range of at least 15 μm to allow a substrate layer to function as an insulating layer. For example, each electrode 31a and 31b of the impedance sensor 110 may be designed such that variable A is 0.8 mm, variable B is 6 mm, variable C is 0.3 mm, and variable D is 0.1 mm. However, the present disclosure is not limited thereto, and a distance between the electrodes, the thickness of the electrodes, and the like, may be adjusted by taking into account an analysis target object, a component to be analyzed, the size of the apparatus 1 for analyzing a biological material component, the amount of blood sample if blood is collected and analyzed, and the thickness of a blood vessel if analysis is performed on skin.

Figure 3C:
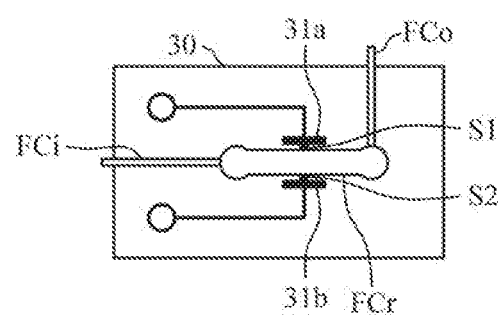

Referring to FIG. 3C, in one embodiment of the impedance sensor 110, a channel capable of storing a fluid may be formed on a main body substrate 30 so that impedance can be measured while flowing the analysis target object in vitro. As shown in FIG. 3C, the channel may include an inlet portion FCi into which the analysis target object is introduced, a storage portion FCr in which the introduced analysis target object is stored, and an outlet portion FCo through which the analysis target object is discharged. The first electrode 31a and the second electrode 31b may be disposed to face each other such that the contact surface S1 of the first electrode 31a is in contact with one side of the storage portion FCr and the contact surface S2 of the second electrode 31b is in contact with the other side of the storage portion FCr. In this case, the analysis target object may be blood acquired from a subject using a noninvasive method or a sample solution that is simulated to have physical characteristics of blood.

Figure 3D:
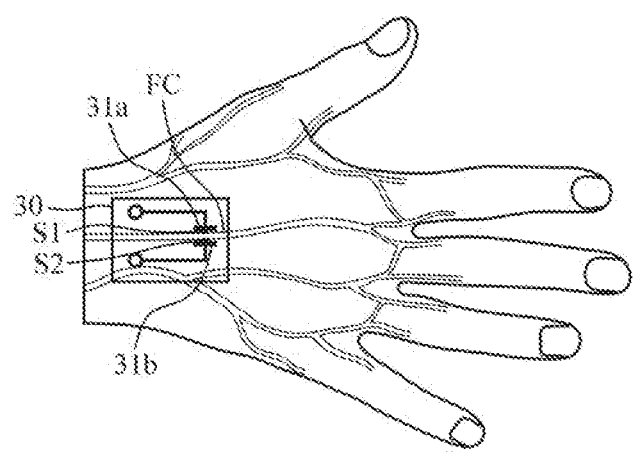

Referring to FIG. 3D, another embodiment of the impedance sensor 110 may be configured to measure impedance of blood in vivo. In this case, the analysis target object FC may be blood flowing in a blood vessel of a human body. FIG. 3D shows a region where blood vessels are present on the back of a human hand, but is not limited thereto, and any portion of a human body at which bio-impedance can be measured is possible. The first electrode 31a and the second electrode 31b of the impedance sensor 110 may be disposed in various forms on a substrate 30 to allow the impedance measurement on region where a blood vessel is present in the subject. For example, as shown in the drawings, the first electrode 31a and the second electrode 31b may be disposed to face each other at a distance such that the contact surfaces S1 and S2 can be in contact with the exterior of the blood vessel. The arrangement form of the first electrode 31a and the second electrode 31b may not be particularly limited, and they may be modified and manufactured in various forms in consideration of a site to be tested, characteristics of each user, a type of biological material component, and the like.

Referring to FIGS. 1 and 2, the processor 200 may control various operations of the apparatuses 1 and 2 for analyzing a biological material component. For example, the processor 200 may control the impedance measurement assembly 120 when an event of analyzing a biological material component occurs according to a user request or a preset period. The processor 200 may be electrically connected to the impedance measurement assembly 120 and may receive impedance data measured by the impedance measurement assembly 120 to analyze a biological material component. In this case, the biological material component may include blood sugar, cholesterols, triglycerides, proteins, and uric acid, but is not limited thereto.

For example, when a blood sugar condition changes, electrical properties of components of blood (e.g., plasma, red blood cell cytoplasm, and red blood cell membranes) change. In this case, the processor 200 may measure impedance of blood flowing through the apparatuses 1 and 2 for analyzing a biological material component, extract the impedance of the blood using an electrical equivalent model including components of blood, and acquire an electrical property value for each component on the basis of the extracted impedance value of the blood. In addition, the processor 200 may estimate a blood sugar level using the acquired electrical property value for each component.

Figure 4:
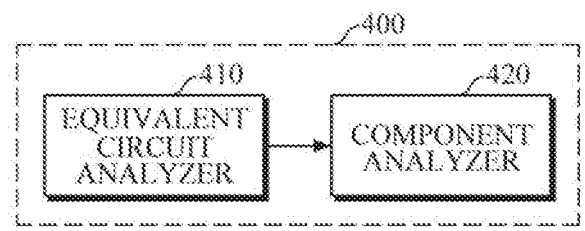
FIG. 4 is a block diagram illustrating one embodiment of a processor of an apparatus for analyzing a biological material component according to an example embodiment.
Figure 5:
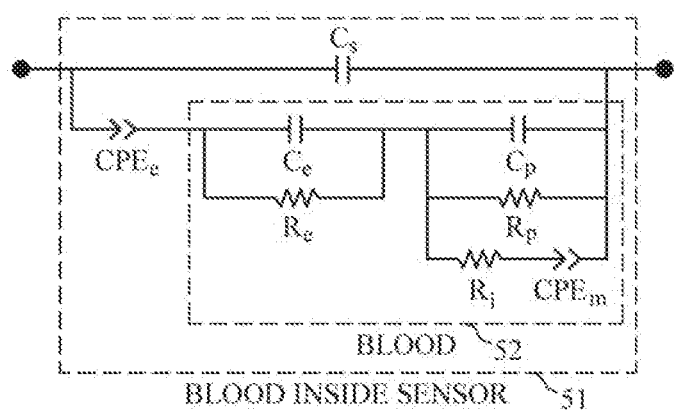
FIG. 5 is a diagram for describing equivalent circuit modeling according to an example embodiment.

FIG. 4 is a block diagram illustrating an example embodiment of the processor 200 of the apparatuses 1 and 2 for analyzing a biological material component. FIG. 5 is a diagram for describing equivalent circuit modeling according to an example embodiment.

Referring to FIG. 4, a processor 400 in an example embodiment may include an equivalent circuit analyzer 410 and a component analyzer 420.

The equivalent circuit analyzer 410 may model measured impedance as an equivalent circuit to extract parameters related to physical characteristics of an analysis target. In this case, the equivalent circuit may include two or more resistors and two or more capacitors. At least some of the two or more capacitors may include a constant phase element (CPE). The CPE is an element that has a characteristic intermediate between a resistor and a capacitor, and may be expressed as shown in Equation 1 below.

$$Z_{CPE} = \frac{1}{C(2\pi f)^{\alpha}} \quad (1)$$

Here, the amplitude of the CPE is represented, f is a frequency, and a is a characteristic intermediate between a resistor and a capacitor, and in the case of human skin, may be a value between, for example, 0.5 and 1.

The equivalent circuit analyzer 410 may deduce noise effects, such as parasitic components or polarization effects, using a material other than a target fluid to be analyzed, such as air, water, a reference solution, or the like. The equivalent circuit analyzer 410 may model the equivalent circuit of impedance measured through the impedance sensor 110 by reflecting the deduced noise effects.

For example, the equivalent circuit analyzer 410 may estimate parasitic components of the impedance sensor 110 using impedance measured through repeated experiments based on the air, water, or reference solution injected instead of the analysis target. In this case, the reference solution may include a conductive solution.

FIG. 5 illustrates an equivalent circuit 51 of raw impedance data measured through the impedance sensor 110 and an equivalent circuit 52 of impedance data in which noise, such as sensor parasitic components or polarization effects, is removed. Raw impedance data measured by changing a frequency may include noise, such as a parasitic component of the impedance sensor 110 and a polarization effect. Referring to FIG. 5, the equivalent circuit analyzer 410 may model the equivalent circuit 51 of the raw impedance data measured through the impedance sensor 110 by including a capacitor representing a parasitic component of the impedance sensor 110 that is previously measured using a material other than the analysis target, for example, air, water, a reference solution, or the like, and a CPE representing a polarization effect.

The equivalent circuit analyzer 410 may extract parameters related to the physical characteristics of the analysis target using the modeled equivalent circuit 51. For example, parameters related to physical characteristics of the analysis target may be acquired from elements constituting the equivalent circuit 52 of blood that remains after removing the parasitic component capacitance Cs and the polarization effect CPEe, which are already known, from the modeled equivalent circuit 51. For example, plasma capacitance Cp, plasma resistance Rp, cytoplasmic resistance (Ri), an amplitude (C in Equation 1 above) of cell membrane CPE CPEm, a property value ($\alpha$ in Equation 1 above), and the like, may be extracted as parameters. In addition, characteristics of equivalent capacitance (Ce) and resistance (Re) in body fluids that represent, respectively, diagonal capacitance and diagonal resistance caused by difficulty in specifying the arrangement of lines of electric force flowing into the blood may be additionally extracted as parameters.

The component analyzer 420 may analyze a biological material component on the basis of six parameters extracted by the component analyzer 420. For example, the component analyzer 420 may extract electrical conductivity values of components of blood (e.g., plasma, red blood cells, cytoplasm, and red blood cell membranes) through the six extracted parameters. In the case of the red blood cell membrane, the electrical conductivity value is close to zero, except for the case where the red blood cell membrane is destroyed by excessive physical and chemical stimulation, and hence it can be assumed to be a fixed value.

The component analyzer 420 may acquire characteristics for analyzing the biological material component on the basis of the extracted parameters.

For example, the component analyzer 420 may acquire one of the predetermined parameter values among the extracted parameter values (e.g., the plasma resistance, the electrical conductivity of the red blood cell membrane, or a combination of two or more parameter values) as the characteristic. For example, it can be seen that as blood sugar increases, the electrical conductivity of the plasma decreases and the electrical conductivity of the cytoplasm increases. Therefore, blood sugar may be estimated using a relationship between the electrical conductivity of the plasma and the electrical conductivity of the cytoplasm.

In another example, when a parameter is extracted, the component analyzer 420 may normalize the extracted parameter based on a parameter at a reference time point and acquire the amount of change in the parameter relative to the reference time point or a combination of two or more parameter change amounts as the characteristic. In this case, the reference time point may include a fasting time point and may be a calibration time point. For example, the component analyzer 420 may normalize the measured parameter by dividing the result of subtracting the parameter value at the reference time point from the measured parameter value by the parameter at the reference time point.

When the characteristic is acquired, the component analyzer 420 may acquire an estimate value of the biological material component by applying a predefined biological material component analysis model to the characteristic. For example, the biological material component analysis model may be an analytic model that defines the relationship between the characteristic and blood sugar. The biological material component analysis model may be a linear functional formula, but is not limited thereto, and may be defined through various methods, such as linear/nonlinear regression analysis, neural networks, deep learning, and the like.

Figure 6:
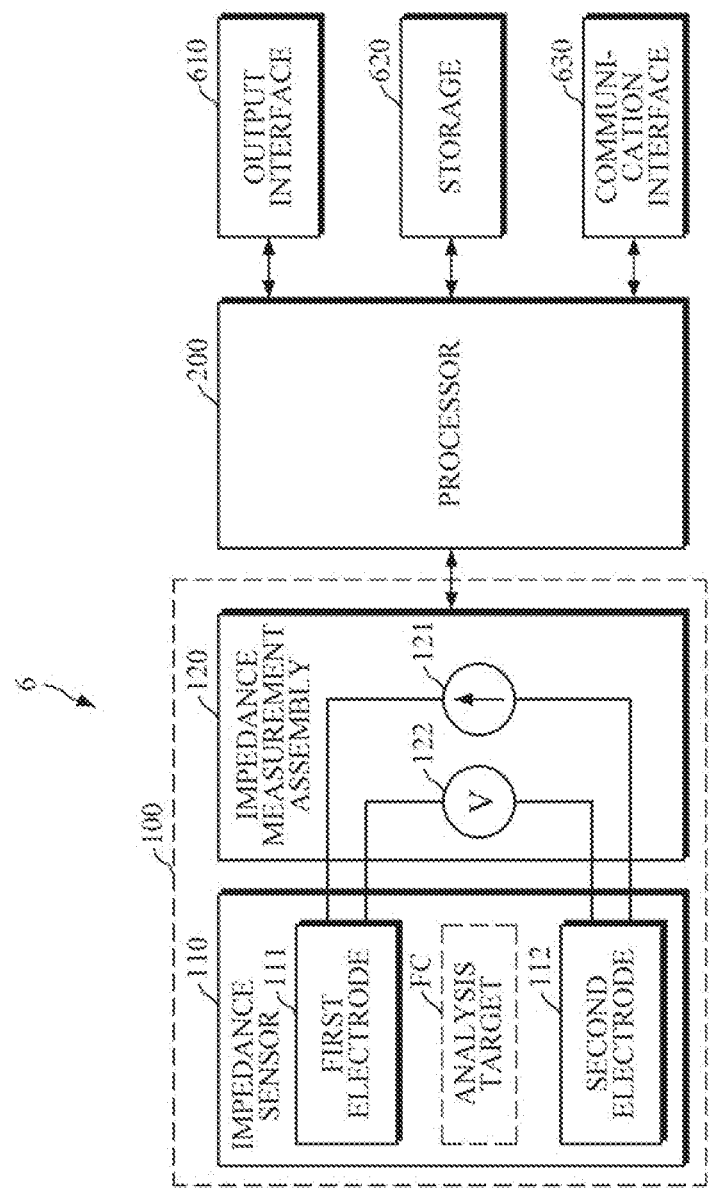
FIG. 6 is a block diagram illustrating an apparatus for analyzing a biological material component according to an example embodiment.

FIG. 6 is a block diagram illustrating an apparatus for analyzing a biological material component according to an example embodiment.

Referring to FIG. 6, an apparatus 6 for analyzing a biological material component may include an impedance sensor 110, an impedance measurement assembly 120, a processor 200, an output interface 610, a storage 620, and a communication interface 630. The impedance sensor 110, the impedance measurement assembly 120, and the processor 200 have been described with reference to FIGS. 1 to 5, and hence detailed descriptions thereof will not be reiterated.

The output interface 610 may provide a processing result of the processor 200 to a user. For example, the output interface 610 may visually output the processing result through a visual output module, such as a display. For instance, the output interface 610 may divide the display into two or more sections and output basic information, such as impedance information used for biological material component analysis, to a first section. In addition, a result of analysis of a biological material component (i.e., an estimate value of the biological material component) may be output to a second section. Biological material component analysis history data for a predetermined period of time in the form of a graph may also be output to the second section, and when the user selects the result of analysis of a biological material component at a specific point in time, basic information and/or other detailed additional information used for the analysis of the biological material component at the specific point in time may be output to the first section. In this case, when the estimate value of the biological material component is outside of a normal range, it may be highlighted in red color or the normal range may be displayed together so as to inform the user that the estimate value of the biological material component is abnormal.

In another example, the output interface 610 may provide the user with the result of analysis of the biological material component in a non-visual manner, such as voice, vibration, and tactile sensation, using a voice output module, such as a speaker, or a haptic module solely or together with a visual display.

The storage 620 may store a variety of reference information for analysis of a biological material component, an impedance measurement result, the result of analysis of the biological material component, and the like. In this case, the reference information may include user characteristic information, such as age, sex, and health condition of a user. Also, the reference information may include parameter values at a reference time point, a biological material component analysis model, and the like.

The storage 620 includes a storage medium of a flash memory type, a hard disk type, a multimedia card micro type, a card type memory (e.g., secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but is not limited thereto.

The communication interface 630 may communicate with an external device to transmit and receive various data related to the biological material component analysis. The external device may include an information processing device, such as a smartphone, a tablet PC, a desktop PC, a notebook PC, or the like.

The communication interface 630 may communicate with the external device using various wired/wireless communication technologies including Bluetooth communication, Bluetooth Low Energy (BLE) communication, near field communication (NFC), wireless local access network (WLAN) communication, Zigbee communication, infrared data association, infrared data association (IrDA) communication, wireless fidelity (Wi-Fi) direct (WFD) communication, ultra wideband (UWB) communication, Ant+ communication, Wi-Fi communication, and third generation (3G) communication, fourth generation (4G) communication, and fifth generation (5G) communication. However, the communication technologies are not limited thereto.

Figure 7:
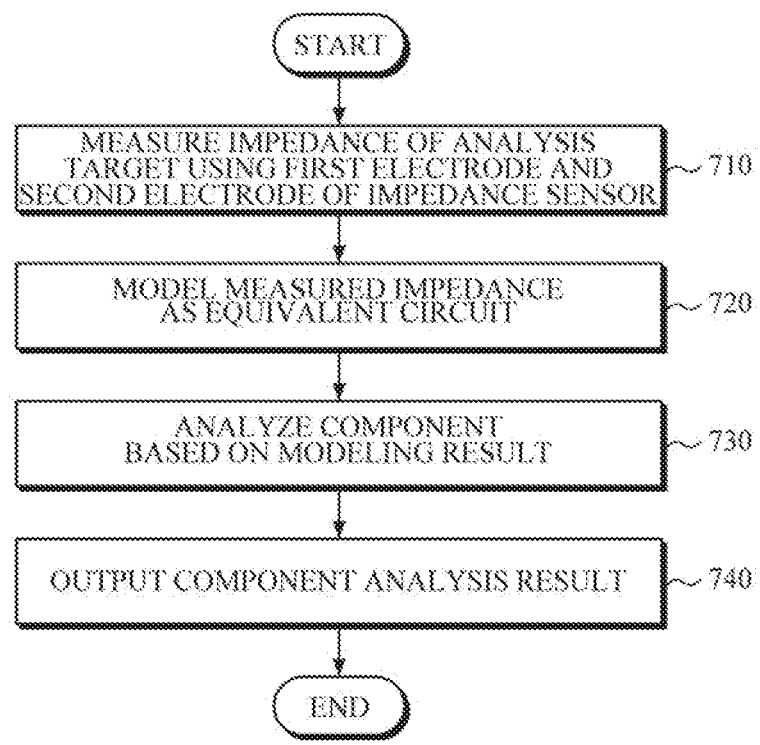
FIG. 7 is a flowchart illustrating a method of analyzing a biological material component according to an example embodiment.

FIG. 7 is a flowchart illustrating a method of analyzing a biological material component according to an example embodiment.

The method of FIG. 7 may be performed by any one of the apparatuses 1, 2, and 6 for analyzing a biological material component shown in FIGS. 1, 2, and 6, respectively.

Referring to FIG. 7, the apparatus 1, 2, or 6 for analyzing a biological material component may measure impedance of an analysis target using the first electrode and the second electrode of the impedance sensor (operation 710). The first electrode and the second electrode may be configured for use in a two-electrode method or a four-electrode method. The first electrode and the second electrode may be disposed to face each other at a distance and each may have a contact surface that has a portion protruding in the shape of a T and is in contact with the analysis target. In this case, when the impedance of the analysis target is measured, characteristics, such as electrode spacing, the thickness of the electrodes, temperature of a fluid, flow rate, and flow velocity, may be adjusted by taking into account a type of the biological material component to be analyzed, the thickness of a blood vessel, the amount of blood, if any is collected, the performance of the device, characteristics of the user, and the ambient measurement environment. A current or a constant voltage may be applied to the first electrode and the second electrode and a current or a voltage imposed on both ends of the first electrode and the second electrode may be measured to measure impedance of the analysis target.

Then, the measured impedance may be modeled as an equivalent circuit (operation 720). The apparatus 1, 2, or 6 for analyzing a biological material component may form an equivalent circuit to include two or more resistors and two or more capacitors. In this case, at least some of the capacitors may include a CPE having a characteristic intermediate between a resistor and a capacitor. In this case, noise effects, such as a parasitic component of the impedance sensor or polarization effects, may be deduced using a material other than blood, such as air, water, a reference solution, or the like, and the deduced parasitic component or polarization effects may be included in an equivalent circuit of pure blood, thereby modeling an equivalent circuit according to the entire sensor environment. In addition, plasma capacitance, plasma resistance, cytoplasm resistance, a value representing the size or inclination of the cell membrane CPE, and additionally characteristics of diagonal capacitance and diagonal resistance caused by difficulty in specifying the arrangement of lines of electrical force flowing into blood may be extracted from the equivalent circuit as parameters.

Then, the biological material component may be analyzed based on the modeling result (operation 730). An estimate value of a biological material component, such as blood sugar, cholesterols, triglycerides, proteins, or uric acid, may be acquired based on six parameters extracted in operation 720. For example, a characteristic may be acquired based on the parameters extracted from the equivalent circuit and the estimate value of the biological material component may be acquired using a biological material component analysis model that defines a relationship between the acquired characteristic and the biological material component.

Then, the result of analysis of the biological material component may be output (operation 750). The result of analysis of the biological material component may be provided to the user in a visual/non-visual manner using various output interfaces, such as a display, a speaker, a haptic device, and the like.

Figure 8:
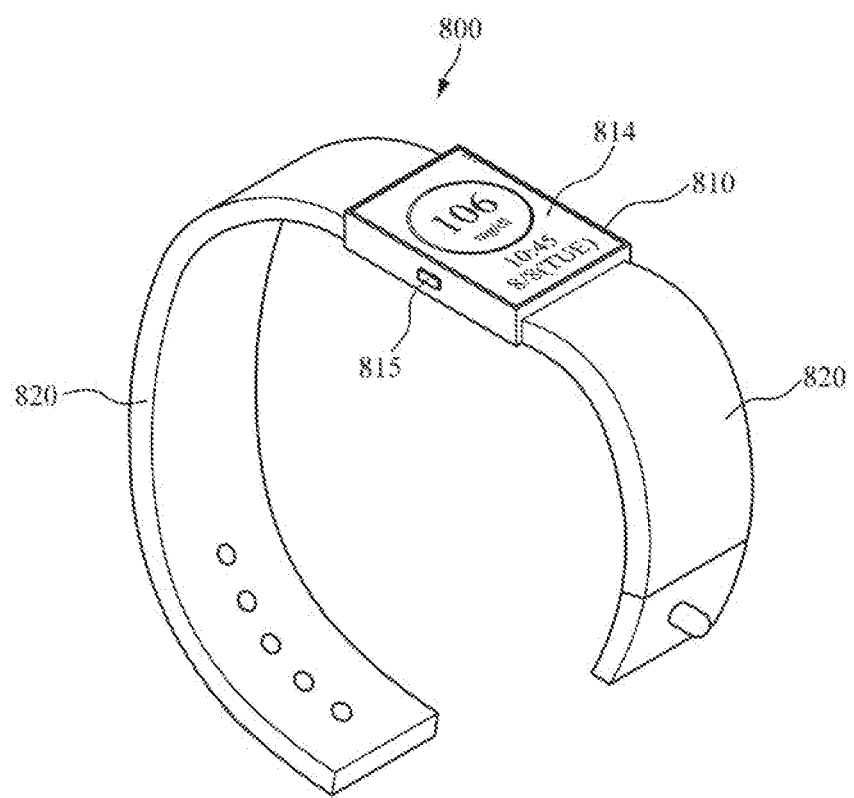
FIG. 8 is a diagram illustrating a wearable device according to an example embodiment.

FIG. 8 is a diagram illustrating a wearable device according to an example embodiment. FIG. 8 illustrates a wearable device, such as a smart watch or a smart band, which is worn on a user's wrist, and any one of the apparatuses 1, 2, and 6 for analyzing a biological material component shown in respectively FIGS. 1, 2, and 6 may be mounted therein.

Referring to FIG. 8, the wearable device 800 includes a main body 810 and a strap 820. Each element of the apparatus 1, 2, or 6 for analyzing a biological material component may be mounted in the main body 810.

The main body 810 may be worn with the strap 820 around the user's wrist and the strap 820 may be formed to be connected at both sides of the main body 810 to be fastened to each other. The strap 820 may be made of a flexible material to enable it to bend around a user's wrist so that the main body 810 may be worn on the user's wrist.

One or more of the main body 810 and the strap 820 may include a battery which supplies power to the wearable device.

The main body 810 may include an impedance sensor which acquires an impedance spectrum at a portion of a user's wrist. The impedance sensor may include a plurality of electrodes, and the electrodes may be disposed to be spaced apart from each other such that each electrode is in contact with each side of the exterior of a blood vessel and measures impedance of blood. However, the present disclosure is not necessarily limited to the region where a blood vessel is present, and any portions, such as the back of a hand, a wrist, a finger, an upper body part, a facial region, and the like, at which bio-impedance measurement is possible may be included.

The main body 810 may include a camera module. The camera module may acquire an image of a subject when the subject is in contact with the main body 810.

The processor may be mounted inside the main body 810, and may be electrically connected to various components, control the various components, and process information collected from the components. For example, when the image of the subject is received from the camera module, the processor may guide the user to a contact position or a contact state.

The processor may analyze a biological material component using the impedance measurement result. The processor may model the measured impedance as an equivalent circuit, extract parameters related to physical characteristics of blood, and estimate blood sugar using the amount of change in the extracted parameter. The equivalent circuit may include two or more resistors and two or more capacitors, and some of the capacitors may include a CPE. In addition, parameters other than parameters of noise-related elements deduced in advance from the modeled equivalent circuit may be extracted from the remaining elements.

The processor may output a result of analysis of the biological material component to the user through a display 814.

The display 814 may be mounted at the top of the main body 810 and may output a variety of information under the control of the processor. Also, the display 814 may include a touch screen enabling touch input and may transmit a user's touch input to the processor.

The communication interface is mounted at the main body 810 and may communicate with an external device. The communication interface may transmit the result of analysis of the biological material component to enable the external device to perform various functions related to monitoring of the user's health condition. The external device may be one of information processing devices, such as a smartphone, a tablet PC, a desktop PC, a notebook PC, and the like, which has a relatively high computing performance.

The wearable device 800 may further include a manipulator 815 which is mounted at the main body 810. The manipulator 815 may be exposed to the outside at one side of the main body 810, may receive a command input from the user, and transmit the received command to the processor. The manipulator 815 may have the function of turning the wearable device on/off.

The example embodiments can be implemented by computer readable code that is stored in a non-transitory computer readable medium, and that is executed by a processor. Code and code segments constituting the computer program can be inferred by a skilled computer programmer in the art. The computer readable medium includes all types of recording media in which computer readable data are stored. Examples of the computer readable medium include a ROM, a RAM, a CD-ROM, a magnetic tape, a floppy disk, and an optical data storage. Further, the computer readable medium may be implemented in the form of a carrier wave such as an Internet transmission. In addition, the computer readable medium may be distributed to computer systems over a network, in which computer readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for analyzing a biological material component, the apparatus comprising:
   an impedance sensor comprising a first electrode having a first contact surface configured to contact an analysis target, and a second electrode having a second contact surface configured to contact the analysis target, the second contact surface facing the first contact surface;
   an impedance measurement assembly configured to measure impedance of the analysis target using the first electrode and the second electrode; and
   a processor configured to model the measured impedance as an equivalent circuit, and analyze a biological material component based on a modeling result,
   wherein the processor is further configured to extract one or more parameters related to characteristics of the analysis target through the modeling result, and
   wherein the one or more parameters include at least one of diagonal capacitance and diagonal resistance.

2. The apparatus of claim 1, wherein the impedance measurement assembly is further configured to measure impedance at a plurality of frequencies in a predefined band.

3. The apparatus of claim 1, wherein the equivalent circuit includes two or more resistors and two or more capacitors.

4. The apparatus of claim 1, wherein the processor is further configured to remove an effect of noise including at least one of a parasitic component of the impedance sensor, and polarization effects from the measured impedance.

5. The apparatus of claim 1, wherein the one or more parameters further include at least one of plasma resistance, cytoplasm resistance, plasma capacitance, and a cell membrane constant phase element (CPE).

6. The apparatus of claim 1, wherein the processor is further configured to acquire an estimate value of the biological material component by applying a predefined biological material component analysis model to the extracted one or more parameters or an amount of change in the one or more parameters relative to a reference time point.

7. The apparatus of claim 6, wherein the reference time point includes a fasting time point.

8. The apparatus of claim 1, wherein the biological material component includes at least one of blood sugar, cholesterols, triglycerides, proteins, and uric acid.

9. The apparatus of claim 1, wherein the analysis target includes blood of a subject or a sample solution that has similar physical characteristics of blood of the subject.

10. The apparatus of claim 1, wherein the impedance sensor further comprises:
    an inlet portion configured to receive the analysis target;
    a storage portion configured to store the analysis target received through the inlet portion; and
    an outlet portion configured to discharge the analysis target stored in the storage portion.

11. The apparatus of claim 1, wherein the impedance sensor further comprises a fluid characteristic adjustment assembly configured to adjust at least one of a temperature of the analysis target and a flow rate of the analysis target.

12. The apparatus of claim 1, wherein each of the first contact surface and the second contact surface have a T shape.

13. A method of analyzing a biological material component, the method comprising:
    measuring impedance of an analysis target using a first electrode having a first contact surface that contacts the analysis target, and a second electrode having a second contact surface that contacts the analysis target, the second contact surface facing the first contact surface;
    modeling the measured impedance as an equivalent circuit; and
    analyzing a biological material component based on a modeling result,
    wherein analyzing the biological material component comprises extracting one or more parameters related to characteristics of the analysis target through the modeling result, and
    wherein the one or more parameters include at least one of diagonal capacitance and diagonal resistance.

14. The method of claim 13, wherein the modeling the measured impedance as the equivalent circuit comprises removing an effect of noise including at least one of a parasitic component of an impedance sensor and polarization effects from the measured impedance.

15. The method of claim 13, wherein the modeling the measured impedance as the equivalent circuit comprises extracting one or more parameters related to characteristics of the analysis target.

16. The method of claim 15, wherein the analyzing the biological material component comprises acquiring an estimate value of the biological material component by applying a predefined biological material component analysis model to the extracted one or more parameters or an amount of change in the one or more parameters relative to a reference time point.

17. The method of claim 13, further comprising adjusting at least one of a temperature of the analysis target and a flow rate of the analysis target.

18. An apparatus for measuring impedance, the apparatus comprising:
    a first electrode having a first contact surface that protrudes from the first electrode, the first contact surface being configured to contact an analysis target;
    a second electrode having a second contact surface that protrudes from the second electrode, being configured to contact the analysis target;
    an impedance measurement assembly configured to measure impedance of the analysis target using the first electrode and the second electrode; and
    a processor configured to extract, from the impedance, one or more parameters related to characteristics of the analysis target through a modeling result,
    wherein the one or more parameters include at least one of diagonal capacitance and diagonal resistance.

19. The apparatus of claim 18, further comprising a fluid characteristic adjustment assembly configured to adjust at least one of a temperature of the analysis target and a flow rate of the analysis target.

* * * * *